United States Patent
La Torre

(10) Patent No.: US 7,947,298 B2
(45) Date of Patent: May 24, 2011

(54) ANIMAL REPELLENT COMPOSITION AND METHOD

(76) Inventor: Gregory A. La Torre, Colonia, NJ (US)

(*) Notice: Subject to any disclaimer, the term of this patent is extended or adjusted under 35 U.S.C. 154(b) by 794 days.

(21) Appl. No.: 11/761,109

(22) Filed: Jun. 11, 2007

(65) Prior Publication Data

US 2007/0248688 A1 Oct. 25, 2007

Related U.S. Application Data

(63) Continuation-in-part of application No. 10/731,658, filed on Dec. 9, 2003, now abandoned.

(60) Provisional application No. 60/446,390, filed on Feb. 12, 2003.

(51) Int. Cl.
*A01N 25/32* (2006.01)

(52) U.S. Cl. .......... 424/406; 424/47; 424/405; 424/407; 424/581; 424/725; 424/731; 424/734; 424/747; 424/750; 424/754; 424/760; 424/775; 514/557; 514/920

(58) Field of Classification Search .................. None
See application file for complete search history.

(56) References Cited

U.S. PATENT DOCUMENTS

| | | | | |
|---|---|---|---|---|
| 4,455,304 | A | * | 6/1984 | Yaralian ................. 424/405 |
| 5,368,866 | A | * | 11/1994 | Loucas ................... 424/581 |
| 6,531,163 | B1 | * | 3/2003 | Bessette et al. ........... 424/747 |
| 7,019,036 | B2 | * | 3/2006 | Hiromoto ................ 514/775 |
| 2003/0060379 | A1 | * | 3/2003 | Souter et al. ............. 510/131 |
| 2006/0263326 | A1 | * | 11/2006 | Weiser .................... 424/74 |

* cited by examiner

*Primary Examiner* — Neil Levy
(74) *Attorney, Agent, or Firm* — Walter J. Tencza, Jr.

(57) ABSTRACT

An animal repellent composition is disclosed that comprises a carrier base and a repellent material. The carrier base and the repellent material are mixed together in a resulting formulation that is used to provide a natural means of deterring unwanted pests and animals from the area in which the composition is used. The composition may also be used as an animal attractant depending on the formulation of the mixed materials. The formulation of the composition can be varied to produce mixtures with different consistencies and properties.

3 Claims, 1 Drawing Sheet

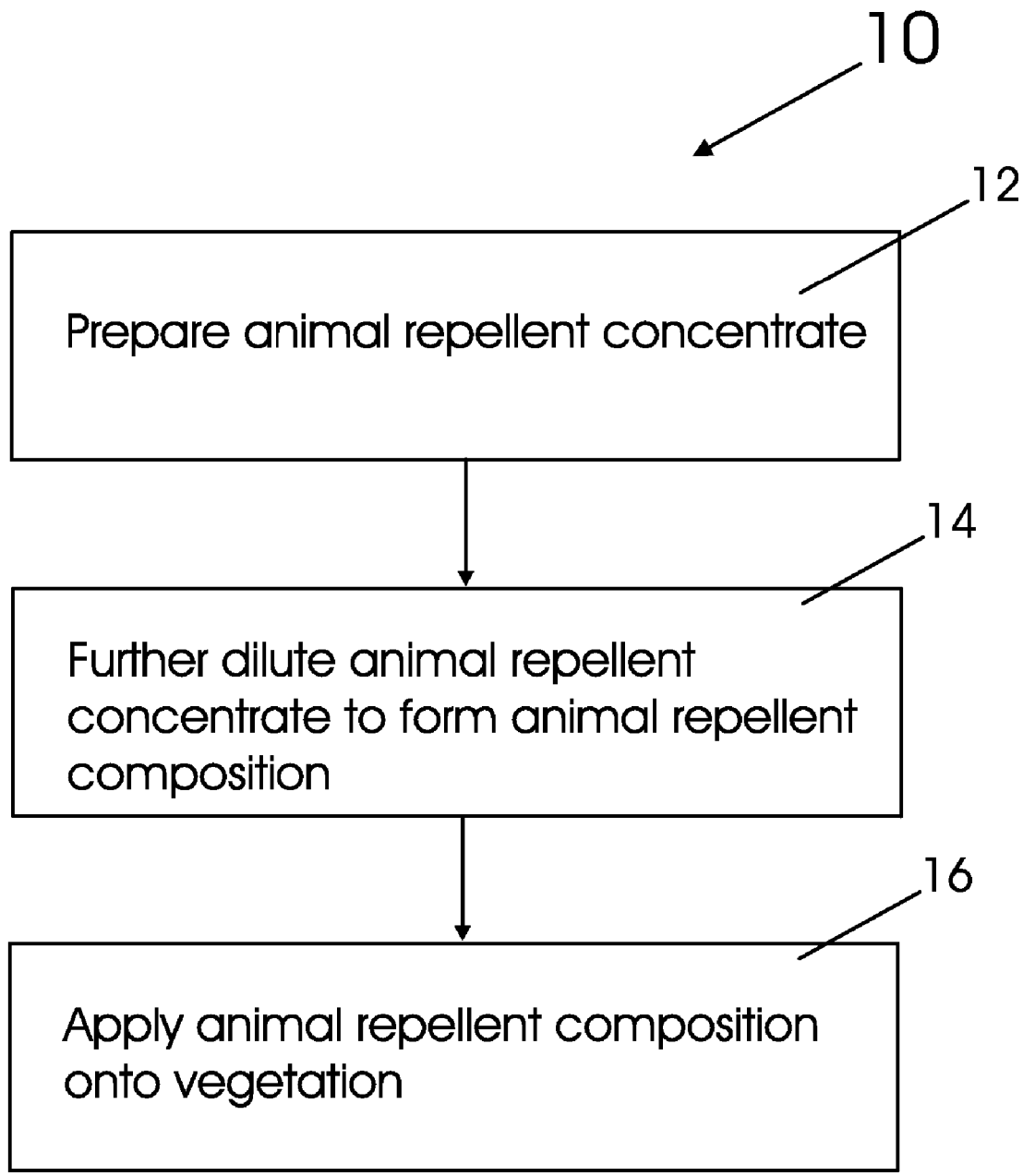

ANIMAL REPELLENT COMPOSITION AND METHOD

CROSS REFERENCE TO RELATED APPLICATION(S)

The present application is a continuation in part of and claims the priority of U.S. patent application Ser. No. 10/731,658, filed Dec. 9, 2003, now abandoned, which claims the priority of provisional patent application Ser. No. 60/446,390 filed on Feb. 12, 2003, inventor Gregory A. La Torre. The present application also claims priority of provisional patent application Ser. No. 60/446,390, filed on Feb. 12, 2003.

FIELD OF THE INVENTION

This invention relates to improved methods and apparatus concerning deterring pests such as deer or rabbits from eating plants.

BACKGROUND OF THE INVENTION

Deer, rabbits, and Canadian geese cause great damage to shrubbery, landscaping, and vegetation in suburban areas as well as on farms. There is a need to protect vegetation from the damage caused by these animals.

SUMMARY OF THE INVENTION

A method is provided, in one embodiment, which includes preparing an animal repellent composition and applying the animal repellent composition onto vegetation. The animal repellent composition typically includes peppermint oil. The peppermint oil repels deer, rabbits and Canadian geese, as well as other pests. The animal repellent composition can be applied by spraying on with any commercial spray device.

An object of the present invention is to provide an all natural biodegradable animal repellent composition, especially for repelling deer, rabbits, and Canadian geese. Typically the animal repellent composition should contain no synthetic ingredients so that the animal repellent composition can be safely applied to all plantings in need of protection from the destructive browsing habits of deer, rabbits and Canadian Geese.

The animal repellent composition can be made to be pleasant smelling to human beings.

In at least one embodiment the animal repellent composition won't wash off during periods of rain or watering.

In at least one embodiment the animal repellent composition is safer for humans and animals compared to products containing potentially harmful synthetic ingredients.

An animal repellent composition in accordance with an embodiment of the present invention offers an organic animal repellent composition that stimulates growth to plantings previously damaged by animals, such as deer and rabbits.

In at least one embodiment of the present invention, an animal repellent composition is provided that will not burn, stain, or leave an unsightly residue when applied.

One embodiment of the present invention includes a method comprising preparing an animal repellent concentrate, diluting the animal repellent concentrate to form an animal repellent composition, typically with water, and applying the animal repellent composition onto vegetation. The animal repellent concentrate may be comprised of peppermint oil, gum arabic, hydrogenated vegetable oil, garlic oil, white pepper, eggs, and vinegar.

BRIEF DESCRIPTION OF THE DRAWINGS

FIG. 1 shows a flow chart of a method in accordance with an embodiment of the present invention.

DETAILED DESCRIPTION OF THE DRAWINGS

FIG. 1 shows a flow chart 10 of a method in accordance with an embodiment of the present invention. The method begins at step 12. At step 12 an animal repellent concentrate is prepared. At step 14, the animal repellent concentrate is further diluted to form an animal repellent composition. At step 16 the animal repellent composition is applied to vegetation.

The animal repellent composition, in one embodiment can be comprised of an all natural mentha piperita or peppermint oil. The animal repellent composition may be used to protect vegetation, plantings, fruits and vegetables, and trees from the destructive eating habits of deer, rabbits & Canadian geese.

In one embodiment, the animal repellent concentrate may be comprised of ten to fifteen ounces of mentha piperita (peppermint oil), five to ten ounces of hydrogenated vegetable oil, one to five ounces of garlic oil, ten to twenty grams of powdered white pepper, and sufficient water to total one hundred and twenty-eight ounces of animal repellent concentrate. Typically ninety-eight (98) to one hundred and twelve (112) ounces of water is sufficient for the animal repellent concentrate. The animal repellent concentrate is then further diluted at a ten to one ratio (ten parts water, to one part concentrate) to formulate the animal repellent composition.

In yet another embodiment, the animal repellent composition may additionally include twenty to thirty ounces of white vinegar.

In another embodiment, the animal repellent composition may additionally include twenty to thirty whole eggs or fifteen to twenty-five ounces of powdered whole eggs.

In another embodiment, the animal repellent composition may additionally include gum arabic as a thickener and a natural sticking/adherent agent.

The animal repellent composition may also include guar gum as a thickener and a natural sticking/adherent agent.

The present inventor, in a test, prepared a mixture or animal repellent composition of one ounce of Mentha Piperita (peppermint oil), one ounce of vegetable oil, one egg and water (typically sixty-four ounces of water for a total of one-half gallon of animal repellent composition), and applied the animal repellent composition to vegetation using a commercial spray device. The repelling of deer and rabbits was immediate and the initial application remained effective for approximately sixty days.

An animal repellent concentrate in accordance with an embodiment A of the present invention may include:
 (a) Twenty ounces (11.25%) of mentha piperita ("menthe piperita" is the biological name for "peppermint oil"),
 (b) Ten ounces (7.5%) of hydrogenated vegetable oil,
 (c) Five ounces (3.75%) of garlic oil,
 (d) Ten teaspoons (0.0035% to 0.0075%) of white pepper,
 (e) Ten teaspoons of Gum Arabic, or between three to five percent of gum Arabic,
 (f) Thirty large eggs (47%) of the animal repellent composition by weight), or twenty-five ounces of powdered eggs, and
 (g) Twenty-five ounces (25%) of white vinegar.

The above concentrate (including ingredients (a)-(g)) can be mixed with water to form an animal repellent composition for spraying. The concentrate (a)-(g), can be mixed with water at a ratio of 12.8 ounces of concentrate to 115 (one hundred fifteen) ounces of water to make one gallon of a ready to use animal repellent composition or mixture.

In one embodiment of the present invention, an animal repellent composition, such as described for embodiment A, is thoroughly applied by a mist or spray from any commercial spray device directly onto the vegetation. The animal repellent composition protects the vegetation from the destructive eating habits of deer, rabbits, and Canadian geese. Generally one application of the animal repellent composition remains effective for a period of three to four months.

If the embodiment A is used, generally one gallon of the ready to use animal repellent composition covers approximately 4,000 square feet.

The strong taste and smell of mentha piperita (peppermint oil) in the animal repellent composition and the burning sensation that occurs while either breathing the animal repellent composition in through the nose or when attempted to be eaten by deer, rabbits, or Canadian geese has been found by the inventor to be extremely offensive to these animals. Furthermore, any plantings and vegetation sprayed with an animal repellent composition in accordance with one or more embodiments of the present invention are no longer eaten by these animals for periods of up to three or four months.

A first test was conducted where two piles of apples were placed approximately twenty-five feet apart. One pile was sprayed with the animal repellent composition of embodiment A, while the other was not. Within 1 hour the test area was visited by seventeen deer. The untreated apples were quickly consumed, while the apples treated with the animal repellent composition remained uneaten. Deer continued visiting this test area twice a day for approximately 30 days and never ate the apples treated with the animal repellent composition of embodiment A.

In another area, a group of deer had previously been visiting and eating the buds from a group of untreated Azaleas on a daily basis. A second test was conducted, in which the Azaleas were sprayed with the animal repellent composition of embodiment A and the results were immediate. The deer continued to pass through that area on a daily basis without eating any of the treated Azalea buds. About forty-five days later and after a recent snow storm there was evidence that deer removed the snow from the top of the treated Azaleas in an attempt to eat the remaining buds, but the buds remained uneaten.

The two geographic areas used in the first and second tests above, were intensely surveyed over quite a few months with various further tests performed under a variety of conditions. In these further tests, the inventor observed no further damage done by browsing deer and rabbits after these areas were treated with the animal repellent composition of embodiment A.

Additional ingredients can be added to the animal repellent composition of embodiment A. The additional ingredients may include lemon grass oil 10 to 15 oz, clove leaf Oil 10 to 15 oz, Ten teaspoons (0.0035% to 0.0075%) of cayenne pepper, castor oil 10 to 15 oz 20 to 30 teaspoons of sodium chloride. The additional ingredients added to the embodiment A to form an embodiment B. The embodiment B has been found to effectively repel deer, rabbits, squirrels, raccoons, mice, rats, opossums, porcupines, and other rodents.

In one embodiment of the present invention, white pepper, garlic oil and peppermint oil blended together with gum arabic and vegetable oil blended together as an all natural adherent sticker are much more effective as a deer repellent than any previous prior art deer repellent.

Gum arabic is particularly useful in accordance with an embodiment of the present invention. The gum arabic used (typically in the percentage of 10 teaspoons) is an incredible sticker that allows an animal repellent composition in accordance with an embodiment of the present invention to remain on plants even during extended periods of heavy rain. No prior art deer repellents have used gum Arabic as an adherent.

In another embodiment, spearmint Oil (mentha spicata) or cornmint oil (mentha arvensis) can be used instead of peppermint oil. Peppermint oil may be too expensive, and in that case, spearmint or cornmint oil can be used. The percentage for the spearmint or cornmint oil can be the same as that which would be used for the peppermint oil. An animal repellent concentrate can be made having between 10 to 20 oz of spearmint or cornmint oil. The concentrate would then be diluted with water Although the invention has been described by reference to particular illustrative embodiments thereof, many changes and modifications of the invention may become apparent to those skilled in the art without departing from the spirit and scope of the invention. It is therefore intended to include within this patent all such changes and modifications as may reasonably and properly be included within the scope of the present invention's contribution to the art.

I claim:

1. A method comprising
    preparing an animal repellent concentrate for repelling deer;
    determining that specific vegetation has been damaged by deer;
    diluting the animal repellent concentrate to form an animal repellent composition;
    applying the animal repellent composition onto the specific vegetation;
wherein the animal repellent concentrate is comprised of the following in approximately the following percentages:
    11.25% peppermint oil,
    7.5% of hydrogenated vegetable oil,
    3.75% of garlic oil
    0.0035% to 0.0075% of white pepper,
    between three and five percent of gum Arabic,
    47% eggs, and
    25% white vinegar; and
    wherein the step of diluting the animal repellent concentrate to form the animal repellent composition comprises diluting the animal repellent concentrate with water in a ratio or about ten parts water by weight to about one part animal repellent concentrate by weight.
2. The method of claim 1 wherein
    the step of applying the animal repellent composition onto vegetation includes spraying.
3. The method of claim 1 wherein
    the animal repellent concentrate is further comprised of lemon grass oil, clove leaf oil, cayenne pepper, onion powder, castor oil, and sodium chloride.

* * * * *